United States Patent [19]

Pociask

[11] 4,052,396

[45] Oct. 4, 1977

[54] PROCESS FOR THE PRODUCTION OF 2-ALKYL OR 2-CYCLOALKYL-4-METHYL-6-HYDROXYPYRIMIDINES

[75] Inventor: Joseph R. Pociask, Greensboro, N.C.

[73] Assignee: Ciba-Geigy Corporation, Ardsley, N.Y.

[21] Appl. No.: 743,555

[22] Filed: Nov. 22, 1976

[51] Int. Cl.$^2$ ............................................ C07D 239/02
[52] U.S. Cl. ................................. 260/251 R; 424/251
[58] Field of Search ..................................... 260/251 R

[56] References Cited

U.S. PATENT DOCUMENTS

| | | | |
|---|---|---|---|
| 3,703,518 | 11/1972 | Inoi et al. | 260/561 N |
| 3,997,536 | 12/1976 | Boller et al. | 260/251 R |
| 4,001,232 | 1/1977 | Groegler et al. | 260/251 R |
| 4,012,506 | 3/1977 | Balke et al. | 260/251 R |

*Primary Examiner*—Donald G. Daus
*Assistant Examiner*—Jose Tovar
*Attorney, Agent, or Firm*—Karl F. Jorda

[57] ABSTRACT

Production of 2-alkyl or 2-cycloalkyl-4-methyl-6-hydroxy pyrimidines by first reacting diketene and lower alkanoic or cycloalkanoic acid nitriles in the presence of catalytic amounts of Bronsted or Lewis acids, followed by treating the diketene/nitrile reaction product with ammonia in the presence of acid catalysts.

8 Claims, No Drawings

PROCESS FOR THE PRODUCTION OF 2-ALKYL OR 2-CYCLOALKYL-4-METHYL-6-HYDROX-YPYRIMIDINES

DETAILED DISCLOSURE

The present invention relates to a new and improved manufacturing process for 2-alkyl or 2-cycloalkyl-4-methyl-6-hydroxypyrimidines of the general formula

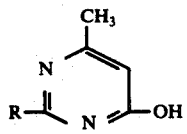

(I)

wherein R represent an alkyl or a cycloalkyl group.

Alkyl groups denoted by R are straight-chain or branched-chain groups having preferably 1 to 4 carbon atoms, such as, methyl, ethyl, n-propyl, isopropyl, n-butyl, secondary butyl, isobutyl or tertiary butyl.

Cycloalkyl groups denoted by R have 3 to 6 ring carbon atoms. Preferred cycloalkyl groups are cyclopropyl, cyclopentyl or cyclohexyl.

The compounds of formula I have particular importance as intermediates for the preparation of, e.g., phosphoric acid esters of substituted hydroxypyrimidines as disclosed and claimed in U.S. Pat. No. 2,754,243 and, in particular, O,O-diethyl-O-(2-isopropyl-4-methyl-6-pyrimidyl)-thiophosphate (DIAZINON), which has great commercial value by virtue of its well-established insecticidal and acaricidal activity and consequent usefulness in pest control.

These substituted hydroxypyrimidines have been produced in commercial practice in a laborious multi-step manner as follows:

a) Iminoether Step:

R—C≡N + C$_2$H$_5$OH + 2 HCl ⟶

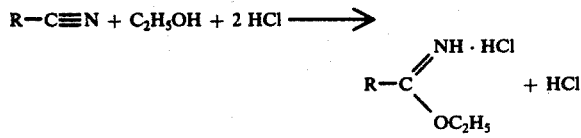

b) Amidine Step:

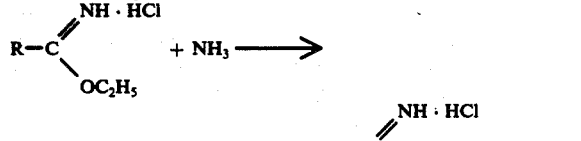

c) Ring-closure Step:

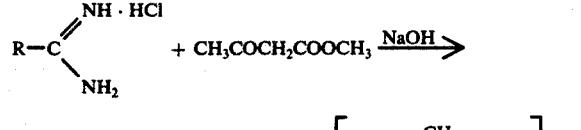

d) Neutralization Step:

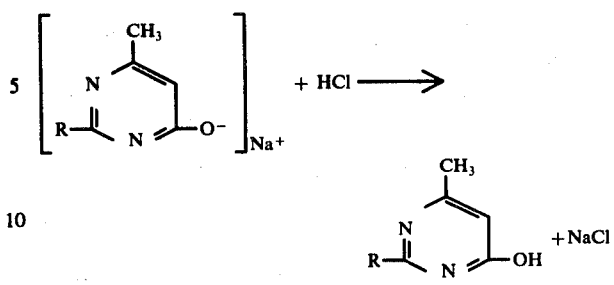

In the above formulae R has the same meaning as given for formula I.

More recently, this conventional manufacturing process has been improved and optimized by way of a continuous ring-closure/neutralization process as disclosed and claimed in U.S. Pat. No. 4,014,879, granted 3/29/77 and alternate processes for the preparation of the subject hydroxypyrimidines have been published in the Japanese patent literature.

For instance, according to Japanese Patent 557,103, the subject hydroxypyrimidines can be prepared by various heat treatments from β-acylaminocrotonamides which are made from β-aminocrotonamide (derived from diketene and ammonia) and acid anhydrides or acid halides and according to published Japanese Patent Application SHo 48-39,942, they can be produced by reacting β-aminocrotonamide and an organic acid ester in the presence of certain alkaline reactants, such as, alkali metals or alkali metal alcoholates.

However, all of these prior art procedures leave something to be desired from the standpoint of efficient and economical large-scale commercial manufacturing.

In the search for better and cheaper process technology for the manufacture of the subject hydroxypyrimidines and the phosphoric acid ester derivatives made therefrom, it has now been found, surprisingly and unexpectedly — and this forms the principal object of this invention — that these hydroxypyrimidines can be synthesized in a completely novel way which involves fewer steps, milder conditions, simpler equipment and less expensive reactants. It has been found that this can be accomplished by reacting diketene and lower alkanoic or cycloalkanoic acid nitriles in a solvent and in the presence of an acid catalyst to form a first-step reaction product, i.e., intermediates which are N-acetoacetyl substituted (lower) alkanoic or cycloalkanoic acid amides but also include acid-catalyzed reaction products of appropriate nitriles and diketene capable of being converted to the subject hydroxypyrimidines by reaction with ammonia, which intermediates are then converted by ammonia to the subject hydroxypyrimidines again in a solvent and in the presence of a catalyst in accordance with the following reaction scheme:

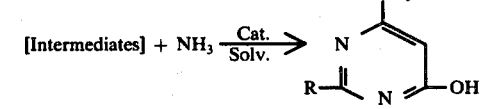

Again, R in the above formulae has the same meaning as given for formula I above.

More specifically, in this novel and improved process, diketene and the lower alkanoic or cycloalkanoic acid nitrile (hereinafter "nitrile") are first reacted to yield, as mentioned above, certain intermediates. This reaction is carried out in an organic solvent and in the presence of catalytic amounts of Lewis and Bronsted acids.

With respect to the specific reaction procedure and especially the order of addition of the reactants, it is advantageous to add diketene slowly to an appropriate reaction vessel containing a solution or suspension, heated to an elevated temperature, of the nitrile and the catalyst. Alternatively, diketene, nitrile, solvent and catalyst are simply mixed together also in a conventional reaction vessel at room temperature before heating to an elevated temperature. Additionally, the catalysts can be added to the reaction mixture in incremental amounts.

The starting materials for this inventive process, diketene and nitrile which are commercially available or accessible, are generally employed in equimolar amounts. However, excess amounts of either reactant, up to about 200 mole % excess, especially of the nitrile can be employed for the purpose of yield improvement.

The reaction time for this diketene/nitrile reaction is typically from about an hour to about eighteen hours, and preferably about 6 to 10 hours.

The organic solvent useful in this diketene/nitrile step can be selected from classes which include, but are not limited to, the following: aromatic hydrocarbons, such as, benzene, toluene, xylene, chlorobenzene, nitrobenzene; chlorinated hydrocarbons, such as, chloroform, carbon tetrachloride, ethylene dichloride, trichloroethylene; tetrachloroethylene; lower alkanoic acids and esters thereof, such as, acetic acid, propionic acid, isobutyric acid, ethyl acetate, ethyl propionate, isobutyl isobutyrate; ethers, such as, ether, tetrahydrofuran, p-dioxane, 1,2-dimethoxyethane; and ketones, such as, methyl ethyl ketone, methyl isobutyl ketone, cyclohexanone; or mixtures thereof.

As Bronsted acids can be enumerated, without limiting them thereto, the following mineral and organic acids: hydrogen chloride, sulfuric acid, phosphoric acid, acetic acid, trifluoroacetic acid, isobutyric acid, p-toluenesulfonic acid. Lewis acids can be illustrated by, but are not limited to, the following acids: boron trifluoride etherate, zinc chloride, aluminum chloride.

Typically, about 5 to 200 mole % of the catalyst per mole of diketene and nitrile is employed and preferably about 10 to 30 mole %.

The reaction temperature in this step can vary within the range of about 20° C to 150° C and preferably between about 25° C and 90° C. It depends often on the solvent chosen.

The second step which involves treating the reaction product of the diketene/nitrile reaction, with or without isolation, with ammonia also in a solvent and in the presence of a catalyst and at elevated temperatures, accomplishes amination and cyclization of the first-step reaction product to 2-alkyl or 2-cycloalkyl-4-methyl-6-hydroxypyrimidine.

More specifically, this second step, where the first-step reaction product is recovered in a conventional manner is carried out by dissolving this reaction product in a heated or refluxing solvent containing the catalyst, followed by sparging in ammonia and accompanied by removal of water, for example, by azeotropic distillation. The conversion of the first-step reaction product to the desired hydroxypyrimidine is almost quantitative.

While amination proceeds rapidly and is completed in a matter of minutes, e.g., 5 to 30 minutes as determined by thin layer chromatography, cyclization takes longer and may be completed only after 1 to 6 hours.

As solvents or solvent system there can be used not only the same solvents or same solvent system that can be employed in the first step as enumerated or mentioned above but also such additional classes as aliphatic alcohols, e.g., isobutanol, tertiary butanol, etc. Particularly preferred is toluene.

With respect to the catalysts, it is advantageous to employ acidic substances, i.e., Bronsted acids, such as, acetic acid, trifluoroacetic acid, isobutyric acid, p-toluenesulfonic acid, phosphoric acid and, most preferably, acetic acid and p-toluenesulfonic acid. However, the second-step reaction proceeds also without acid catalyst.

The acidic catalysts when used as is preferable, are employed in catalytic amounts which typically range between about 25 to 100 mole % per mole of intermediate and preferably between about 30 to 50 mole %.

The reaction temperature in this second step can vary within the range of about 80° to 150° C and preferably between about 95° to 115° C.

It is also entirely feasible to practice the present inventive process in one reactor without isolation and recovery of the first-step reaction product. Furthermore, it is feasible to practice this process in a semicontinuous as well as continuous fashion.

Isolation and recovery of the desired final product, the 2-alkyl or 2-cycloalkyl-4-methyl-6-hydroxypyrimidine, is carried out and effected in accordance with standard chemical procedures.

It should be understood that various changes and modifications in the procedures described above generally and exemplified below specifically can be made, such changes and modifications being within the scope of the appended claims. It should further be understood that the following example illustrating specific embodiments is not intended to limit the disclosure.

EXAMPLE

Hydrogen chloride was bubbled into a 0°–10° C solution of 8.4 g of diketene and 6.9 g of isobutyronitrile in 10 ml of ether for 1.5 hr. The mixture was stirred at ambient temperature for 16 hr., either distilled from the reaction mass at reduced pressure and 100 ml of toluene added to the solid residue. The resulting slurry was refluxed while ammonia gas was bubbled into it for two hours. After addition of 100 ml of chloroform, the mixture was filtered and the filtrate concentrated to 9.0 g of yellow solid containing 40.3% of 2-isopropyl-4-methyl-6-hydroxypyrimidine.

If in the above process wherein the isopropyl embodiment has been illustrated, cyclopropane carboxylic acid nitrile is employed in lieu of isobutyronitrile, 2-cyclopropyl-4-methyl-4-hydroxypyrimidine is obtained in an analogous manner.

What is claimed is:

1. A process for the preparation of 2-alkyl or 2-cycloalkyl-4-methyl-6-hydroxypyrimidine of the formula

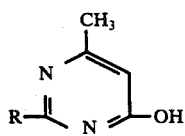

wherein R represents alkyl of 1 to 4 carbon atoms and cycloalkyl of 3 to 6 carbon atoms, which comprises
1. reacting diketene and a nitrile of the formula

RCN wherein R has the same meaning as given above, in an organic solvent at a temperature ranging from about 20° C to 150° C and in the presence of a catalytic amount of a Lewis or Bronsted, acid, and
2. reacting the reaction product obtained in the first step with ammonia in an organic solvent at a temperature ranging from about 80° to 150° C and in the presence or absence of a Bronsted acid.

2. A process according to claim 1, wherein R is isopropyl.
3. A process according to claim 1, wherein the solvent is ether in step 1) and toluene or trichloroethylene in step 2).
4. A process according to claim 1, wherein the catalyst in step 1) is hydrogen chloride.
5. A process according to claim 1, wherein the catalyst in step 2) is acetic acid or p-toluenesulfonic acid.
6. A process according to claim 1, wherein the reaction temperature is between 25° and 90° C in step (1) and about 90° and 115° C in step (2).
7. A process according to claim 1, which is carried out in one reactor without isolation of the first-step reaction product.
8. A process according to claim 1 wherein R is isopropyl, the solvent is ether in step (1) and toluene in step (2), the catalyst is hydrogen chloride in step (1) and acetic acid in step (2) and the temperature is between 25° and 90° C in step (1) and about 95° and 115° C in step (2).

* * * * *